US012582435B2

(12) United States Patent
Vu et al.

(10) Patent No.: US 12,582,435 B2
(45) Date of Patent: Mar. 24, 2026

(54) RETRACTABLE PROTECTION AND/OR SENSING FEATURES FOR POWERED SURGICAL CUTTING DEVICES AND SYSTEMS

(71) Applicant: Medtronic PS Medical, Inc., Fort Worth, TX (US)

(72) Inventors: Michael Vu, Grand Prairie, TX (US); Aayush Malla, Fort Worth, TX (US); Milton F. Barnes, Grand Prairie, TX (US); John W. Kulas, Euless, TX (US); Sophie A. Pervere, Dallas, TX (US)

(73) Assignee: Medtronic PS Medical, Inc., Goleta, CA (US)

( * ) Notice: Subject to any disclaimer, the term of this patent is extended or adjusted under 35 U.S.C. 154(b) by 340 days.

(21) Appl. No.: 18/140,895

(22) Filed: Apr. 28, 2023

(65) Prior Publication Data

US 2023/0346421 A1 Nov. 2, 2023

Related U.S. Application Data

(60) Provisional application No. 63/337,203, filed on May 2, 2022.

(51) Int. Cl.
*A61B 17/3211* (2006.01)
*A61B 17/00* (2006.01)
(52) U.S. Cl.
CPC . *A61B 17/3211* (2013.01); *A61B 2017/00106* (2013.01); *A61B 2017/32113* (2013.01)

(58) Field of Classification Search
CPC .............. A61B 17/3211; A61B 17/326; A61B 17/3209; A61B 17/3494; A61B 17/3496; A61B 17/32002; A61B 17/320016; A61B 2017/320052; A61B 2090/08021; A61B 17/1633; A61B 17/1695
See application file for complete search history.

(56) References Cited

U.S. PATENT DOCUMENTS

| | | | |
|---|---|---|---|
| 6,645,218 B1 | 11/2003 | Cassidy et al. | |
| 6,824,552 B2 | 11/2004 | Robison et al. | |
| 7,077,845 B2 | 7/2006 | Hacker et al. | |
| 7,244,263 B2 | 7/2007 | Robison et al. | |
| 7,674,263 B2 | 3/2010 | Ryan | |
| 7,699,846 B2 | 4/2010 | Ryan | |
| 7,719,437 B2 | 5/2010 | Bertram, III | |

(Continued)

*Primary Examiner* — Brigid K Byrd
(74) *Attorney, Agent, or Firm* — Carter, DeLuca & Farrell LLP

(57) ABSTRACT

A surgical cutting device includes a handle, a shaft assembly extending distally from the handle, a cutting tool extending through the shaft assembly, and a retractable shield. The retractable shield and/or the cutting tool is movable relative to the other between a retracted position, wherein a distal tip of the cutting tool extends through and distally beyond a ring (or other opening) of the retractable shield, and one or more extended positions, wherein the ring (or other portion) of the retractable shield extends distally beyond the distal tip of the cutting tool. In aspects, a sensor is disposed on a distal face of the retractable shield. In aspects, a surgical system including the surgical cutting device includes control circuitry configured to receive sensed data from the sensor and to provide an output based thereon.

19 Claims, 17 Drawing Sheets

(56) References Cited

U.S. PATENT DOCUMENTS

| | | | |
|---|---|---|---|
| 7,803,170 | B2 | 9/2010 | Mitusina |
| 7,854,736 | B2 | 12/2010 | Ryan |
| 7,942,880 | B2 | 5/2011 | Bertram, III |
| 7,993,360 | B2 | 8/2011 | Hacker et al. |
| 8,052,706 | B2 | 11/2011 | Mitusina |
| 8,057,500 | B2 | 11/2011 | Mitusina |
| 8,142,464 | B2 | 3/2012 | Mitusina |
| 8,366,559 | B2 | 2/2013 | Papenfuss et al. |
| 8,808,375 | B2 | 8/2014 | Bertram, III |
| 8,852,191 | B2 | 10/2014 | Bertram, III |
| 8,870,893 | B2 | 10/2014 | Makower et al. |
| 8,944,926 | B2 | 2/2015 | Kramer et al. |
| 9,198,685 | B2 | 12/2015 | Edwards et al. |
| 9,381,032 | B2 | 7/2016 | Edwards et al. |
| 9,474,541 | B2 | 10/2016 | Zider et al. |
| 9,486,232 | B2 | 11/2016 | Heisler et al. |
| 9,517,076 | B2 | 12/2016 | Papenfuss |
| 9,603,607 | B2 | 3/2017 | Papenfuss |
| 9,668,751 | B2 | 6/2017 | Papenfuss |
| 9,775,967 | B2 | 10/2017 | Hatta et al. |
| 9,808,867 | B2 | 11/2017 | Krause et al. |
| 9,833,249 | B2 | 12/2017 | Bertram, III |
| 9,839,441 | B2 | 12/2017 | Hayes et al. |
| 10,179,002 | B2 | 1/2019 | Wasicek et al. |
| 10,271,830 | B2 | 4/2019 | Papenfuss et al. |
| 10,492,800 | B2 | 12/2019 | Papenfuss |
| 10,524,820 | B2 | 1/2020 | Algawi et al. |
| 10,743,912 | B2 | 8/2020 | Papenfuss |
| 10,779,806 | B2 | 9/2020 | Kieturakis et al. |
| 11,020,139 | B2 | 6/2021 | Curtin et al. |
| 11,064,980 | B2 | 7/2021 | Papenfuss et al. |
| 11,065,012 | B2 | 7/2021 | Edwards |
| 2008/0195128 | A1* | 8/2008 | Orbay ................ A61B 1/00048 |
| | | | 600/183 |
| 2010/0179557 | A1* | 7/2010 | Husted ............. A61B 17/32002 |
| | | | 600/300 |
| 2015/0073449 | A1* | 3/2015 | Nallakrishnan ....... A61F 9/0133 |
| | | | 606/167 |
| 2016/0120553 | A1* | 5/2016 | Xie ...................... A61B 17/162 |
| | | | 606/80 |
| 2017/0035487 | A1* | 2/2017 | Kadykowski .......... A61B 18/04 |
| 2019/0357924 | A1 | 11/2019 | Papenfuss |
| 2021/0204910 | A1* | 7/2021 | Begg ................... A61B 8/0841 |
| 2022/0133360 | A1 | 5/2022 | Papenfuss et al. |

* cited by examiner

RETRACTABLE PROTECTION AND/OR SENSING FEATURES FOR POWERED SURGICAL CUTTING DEVICES AND SYSTEMS

CROSS REFERENCE TO RELATED APPLICATION

This application claims the benefit of and priority to U.S. Provisional Patent Application No. 63/337,203, filed on May 2, 2022, the entire contents of which are hereby incorporated herein by reference.

FIELD

The present disclosure relates to powered surgical cutting devices and systems and, more specifically, to retractable protection and/or sensing features for powered surgical cutting devices and systems.

BACKGROUND

Powered surgical cutting devices and systems are utilized in a wide variety of surgical procedures to perform various different surgical cutting functions including, for example, drilling, tapping, resection, dissection, debridement, shaving, sawing, pulverizing, and/or shaping of anatomical tissue including bone.

SUMMARY

As used herein, the term "distal" refers to the portion that is being described which is farther from an operator (whether a human surgeon or a surgical robot), while the term "proximal" refers to the portion that is being described which is closer to the operator. Terms including "generally," "about," "substantially," and the like, as utilized herein, are meant to encompass variations, e.g., manufacturing tolerances, material tolerances, use and environmental tolerances, measurement variations, design variations, and/or other variations, up to and including plus or minus 10 percent. To the extent consistent, any of the aspects described herein may be used in conjunction with any or all of the other aspects described herein.

Provided in accordance with aspects of the present disclosure is a surgical cutting device including a handle, a shaft assembly extending distally from the handle and including one or more shafts, a cutting tool extending at least partially through the shaft assembly, and a retractable shield. The cutting tool includes a distal tip extending distally from the shaft assembly. The cutting tool is adapted to connect to a motor configured to drive the distal tip of the cutting tool to cut tissue. The retractable shield includes a body coupled to the shaft assembly, a ring distally spaced from the body, and an arm interconnecting the body and the ring with one another. At least one of the retractable shield or the cutting tool is movable relative to the other between a retracted position, wherein the distal tip of the cutting tool extends through and distally beyond the ring of the retractable shield, and one or more extended positions, wherein the ring of the retractable shield extends distally beyond the distal tip of the cutting tool.

In an aspect of the present disclosure, the at least one shaft of the shaft assembly includes an inner shaft and an outer shaft. In such aspects, the retractable shield may be formed with or engaged to the outer shaft. The outer shaft may be movable relative to the inner shaft to thereby move the retractable shield relative to the cutting tool between the retracted position and the one or more extended positions. Alternatively, the inner shaft and cutting tool may be movable relative to the outer shaft and the retractable shield.

In another aspect of the present disclosure, the inner shaft rotatably supports the cutting tool therein, e.g., with bearings.

In yet another aspect of the present disclosure, a proximal hub is fixed relative to the inner shaft and a proximal collar is disposed about the proximal hub and operably coupled to the outer shaft such that actuation of the proximal collar relative to the proximal hub moves the outer shaft relative to the inner shaft to thereby move the retractable shield relative to the cutting tool between the retracted position and the one or more extended positions.

In still another aspect of the present disclosure, the cutting tool is configured to rotate and/or reciprocate relative to the shaft assembly to cut tissue. In alternative or additional aspects, a motor may be disposed within the handle and configured to operably connect to the cutting tool to drive the movement, e.g., rotation, oscillation, and/or reciprocation, of the cutting tool.

In still yet another aspect of the present disclosure, the ring of the retractable shield is coaxially positioned about a longitudinal axis defined through the cutting tool and the arm of the retractable shield is radially spaced from and parallel to the longitudinal axis of the cutting tool.

In another aspect of the present disclosure, the retractable shield is releasably engagable with the shaft assembly. Alternatively or additionally, the shaft assembly and the cutting tool are releasably engagable with the handle.

Another surgical cutting device provided in accordance with the present disclosure includes a handle, a shaft assembly extending distally from the handle and including at least one shaft, a cutting tool extending at least partially through the shaft assembly, a retractable shield, and a sensor. The cutting tool includes a distal tip extending distally from the shaft assembly and is adapted to connect to a motor configured to move the distal tip of the cutting tool upon activation thereof. The retractable shield defines a distal face surrounding an opening extending through at least a portion of the retractable shield. The retractable shield is coupled to the shaft assembly and at least one of the retractable shield or the cutting tool is movable relative to the other between a retracted position, wherein the distal tip of the cutting tool extends through the opening and distally from the retractable shield, and one or more extended positions, wherein the retractable shield extends distally beyond the distal tip of the cutting tool. The sensor is disposed on the distal face of the retractable shield.

In an aspect of the present disclosure, the sensor is a video or ultrasound image sensor. Alternatively, the sensor is a nerve sensor, an impedance sensor, or a force sensor.

In another aspect of the present disclosure, the retractable shield includes a body coupled to the shaft assembly, a ring distally spaced from the body, and an arm interconnecting the body and the ring with one another. In such aspects, the opening extends through the ring and the distal face is defined on at least one of the ring or the arm.

In another aspect of the present disclosure, the retractable shield includes a conical body. In such aspects, the opening extends through the conical body and the distal face is defined on the conical body.

A surgical system provided in accordance with the present disclosure includes a surgical cutting device, a sensor, and control circuitry. The surgical cutting device includes a motor, a cutting tool operably coupled to the motor for driving a distal tip of the cutting tool to cut tissue upon activation thereof, and a retractable shield defining a distal face surrounding an opening extending through at least a portion of the retractable shield. At least one of the retractable shield or the cutting tool is movable relative to the other between a retracted position, wherein the distal tip of the cutting tool extends through the opening and distally from the retractable shield, and one or more extended positions, wherein the retractable shield extends distally beyond the distal tip of the cutting tool. The sensor is disposed on the distal face of the retractable shield. The control circuitry is configured to receive sensed data from the sensor and to provide an output based thereon.

In an aspect of the present disclosure, the output includes a determination made by the control circuitry based on the sensed data. In aspects, the determination is a type of tissue.

In another aspect of the present disclosure, the output includes a signal to inhibit activation of the motor or to inhibit input of an activation signal to the motor.

In yet another aspect of the present disclosure, the output includes image data for at least one of display on a display screen or use in control of the surgical cutting device, e.g., to move the retractable shield between the extended and retracted positions based on the image data. Other inputs, e.g., navigation data, robotic data, etc., may additionally or alternatively be used with the image data to facilitate control of the surgical cutting device, e.g., to move the retractable shield between the extended and retracted positions and/or to start/stop activation of the cutting too.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
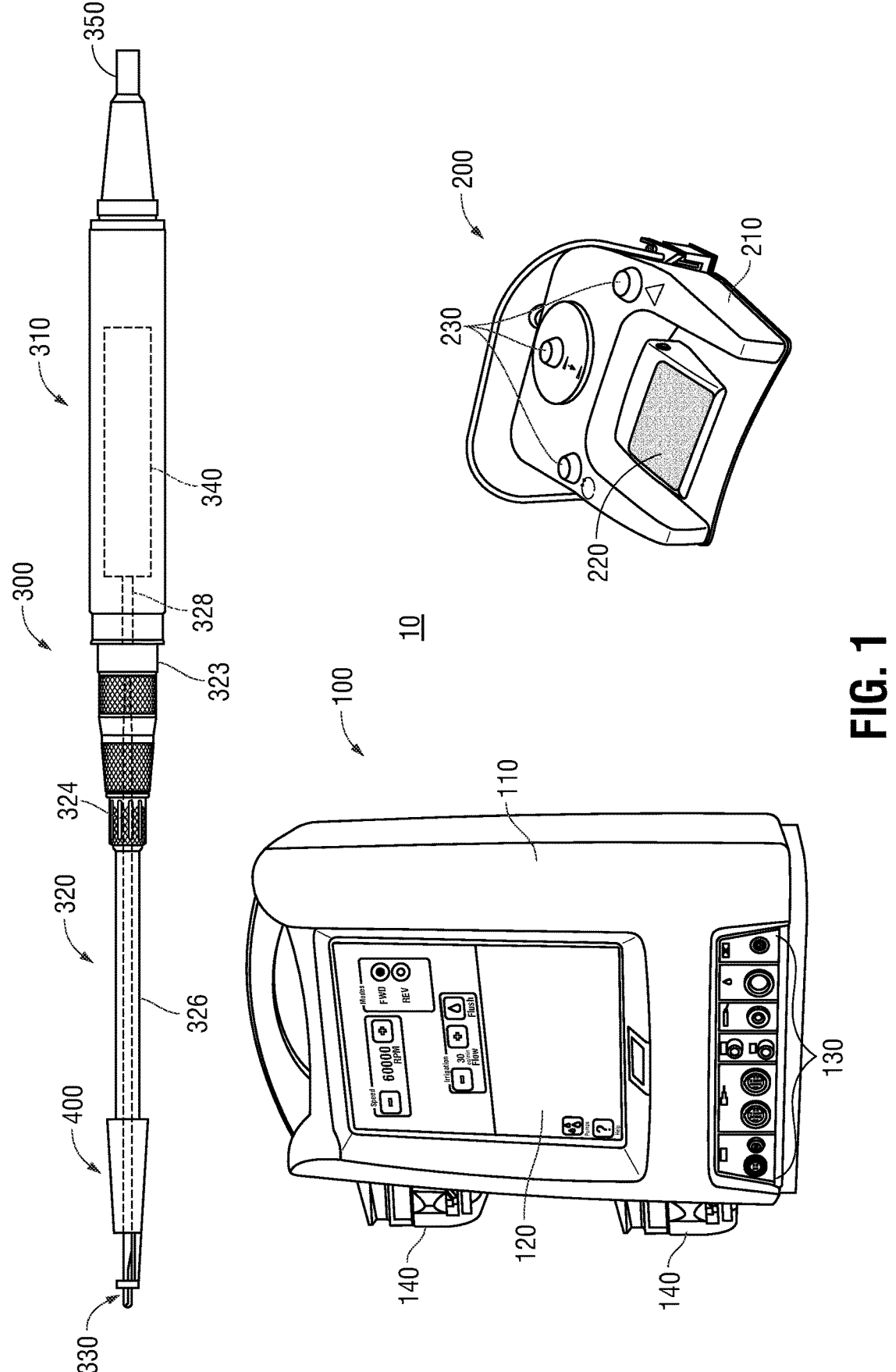
FIG. 1 is a perspective view of a surgical system provided in accordance with the present disclosure including a console, a footswitch, and a powered surgical cutting device.

Turning to FIG. 1, a surgical system 10 provided in accordance with the present disclosure includes a console 100, a footswitch 200, and one or more surgical cutting devices 300. Console 100 may include an outer housing 110 enclosing the internal operable components of console 100, a touch screen graphical user interface (GUI) 120 to receive user input and display information to the user, a plurality of device ports 130, one or more fluid pumps 140, and/or other suitable features. One or more processors and associated memory(s) (not shown) are disposed within outer housing 110 and function to provide power and control signals to devices connected to console 100; to process user inputs, feedback data, and other information received at console 100; and to control the one or more fluid pumps 140. Suitable hardware and drive mechanisms may be disposed within outer housing 110 to perform the various functions of console 100 and may include, for example, power-generating circuitry, sensor circuitry, motors, pump drivers, etc.

Footswitch 200 is configured to connect to one of the device ports 130 of console 100 and includes a base 210, a foot pedal 220 (including an underlying switch or switches (not explicitly shown), and one or more control buttons 230. A cord (not shown) having a plug at the free end is configured to connect footswitch 200 to one of the device ports 130 of console 100 such that user inputs provided to footswitch 200 are received at console 100, e.g., for controlling settings, actuating, and/or otherwise operating one or more devices associated with console 100.

The one or more surgical cutting devices 300 may define any suitable configurations for use in performing various different surgical tasks, for use in various different procedures, etc. One example of a suitable surgical cutting device, surgical cutting device 300, generally includes a handle 310, a shaft assembly 320 extending distally from handle 310 (releasably or integrally connected thereto), a cutting tool 330 extending distally from shaft assembly 320, a motor 340 disposed within handle 310 and operably coupled to cutting tool 330 to drive rotation and/or reciprocation of cutting tool 330 relative to shaft assembly 320 to cut tissue, and a cord 350 to connect motor 340 to console 100 to enable console 100 to power and control motor 340, thereby controlling cutting tool 330. Motor 340 may be an electric motor, pneumatic motor, ultrasonic transducer, or other suitable motor configured to drive cutting tool 330 to rotate and/or reciprocate for cutting tissue. In aspects, surgical cutting device 300 may further include additional features such as, for example, hand control(s), navigation, articulation, etc.

Figure 2:
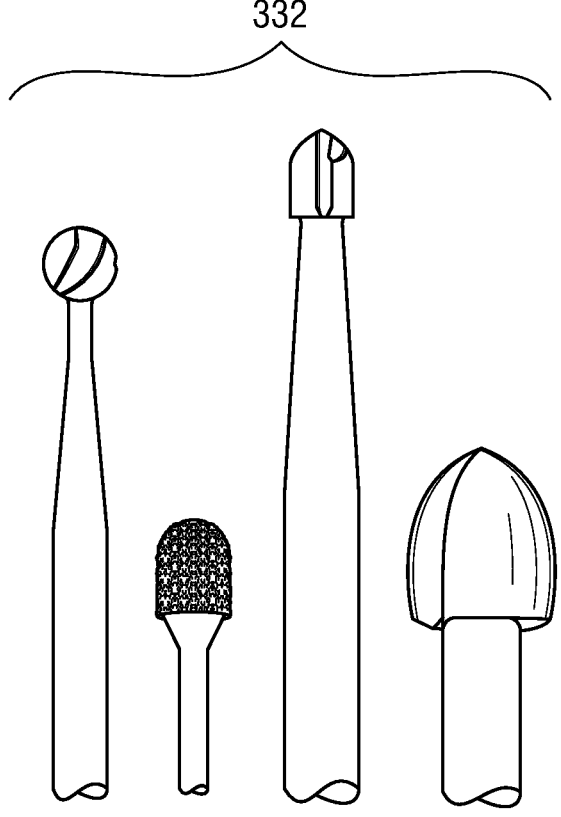
FIG. 2 illustrates various different rotational cutting tips configured for use with the powered surgical cutting device of FIG. 1.

Cutting tool 330 may define any suitable configuration and may be integrated with surgical cutting device 300 or removable therefrom. More specifically, and with additional reference to FIG. 2, various different rotational cutting tools 332 may be configured for releasable attachment with surgical cutting device 300. In aspects, rotational cutting tools 332 are releasably engagable with shaft assembly 320 (which, in turn, may be releasably or integrally connected to handle 310). Alternatively, rotational cutting tools 332 may be integral with corresponding shaft assemblies 320 that are, in turn, releasably engagable with handle 310. In either configuration, surgical cutting device 300 is thus capable of being interchangeably customized with a particular rotational cutting tool 332, depending upon a particular purpose. Reciprocating cutting tools and/or cutting tools configured for both rotation and reciprocation are also contemplated.

Figure 3A:
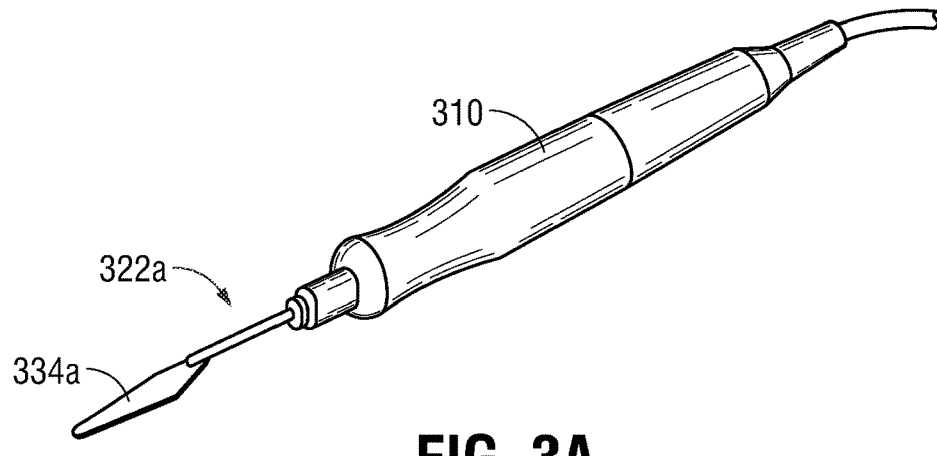
FIGS. 3A-3C are perspective views of various different surgical saw-type powered surgical cutting devices configured for use with the surgical system of FIG. 1.
Figure 3B:
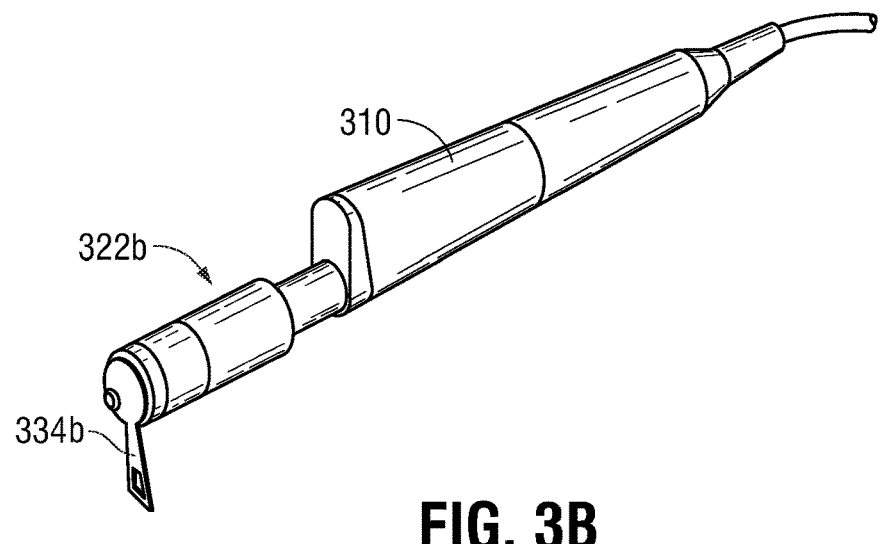
Figure 3C:
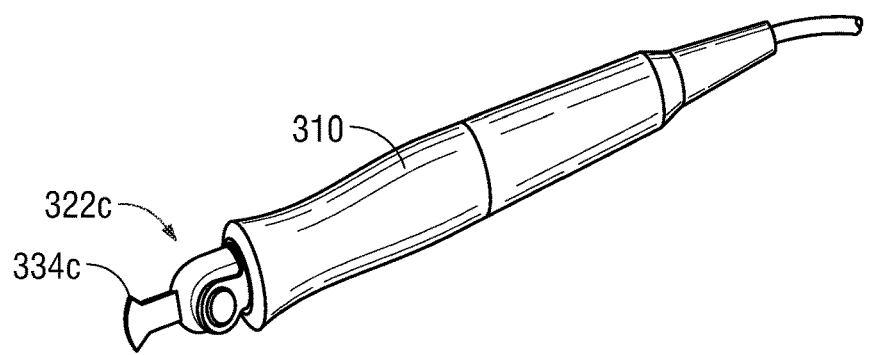
Figures 4A, 4B, 4C:
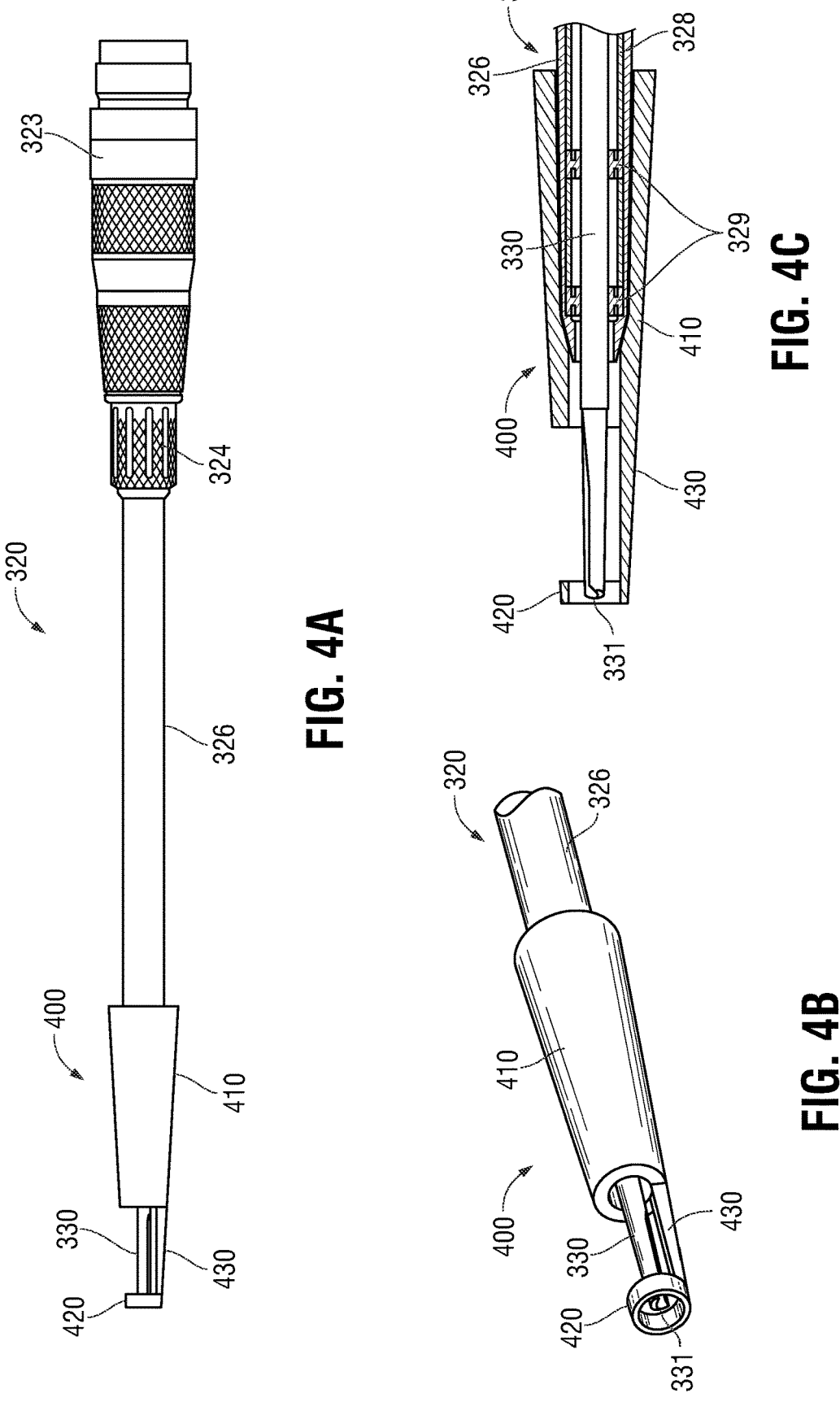
FIG. 4A is a side view of the powered surgical cutting device of FIG. 1 including a retractable shield in accordance with the present disclosure attached thereto and disposed in an extended position.
FIG. 4B is a perspective view of a distal portion of the powered surgical cutting device of FIG. 1 including the retractable shield attached thereto and disposed in an extended position.
FIG. 4C is a longitudinal, cross-sectional view of the distal portion of the powered surgical cutting device of FIG. 1 including the retractable shield attached thereto and disposed in an extended position.

With reference to FIGS. 3A-3C, in addition or as an alternative to rotational cutting tools 332 (FIG. 2), handle 310 may releasably or integrally connect to a shaft assembly 322a, 322b, 322c including a respective saw cutting tool 334a, 334b, 334c configured for longitudinal reciprocating motion along a longitudinal axis of the shaft assembly 322a, reciprocating motion radially about an axis substantially parallel to a longitudinal axis of the shaft assembly 322b, or reciprocating motion radially about an axis substantially perpendicular to a longitudinal axis of the shaft assembly 322c, respectively. Other suitable saw cutting tools are also contemplated.

Referring to FIGS. 4A-5C, shaft assembly 320 of surgical cutting device 300 (FIG. 1) is shown including cutting tool 330 extending distally therefrom and a retractable shield 400 attached thereto. Although detailed with respect to shaft assembly 320 and cutting tool 330, the aspects and features of the present disclosure detailed below are equally applicable for use with the other shaft assemblies and cutting tools detailed herein or any other suitable shaft assemblies and/or cutting tools.

Shaft assembly 320 includes a proximal hub 323 configured to releasably (or, in other aspects, integrally) connect to handle 310 (FIG. 1), a proximal collar 324, an outer shaft 326, and an inner shaft 328. Inner shaft 328 is fixed relative to proximal hub 323 and includes a plurality of bearings 329 configured to rotatably support cutting tool 330 therein, thus permitting rotation of cutting tool 330 relative to inner shaft 328. Cutting tool 330 extends through inner shaft 328 and may be configured for direct or indirect coupling with motor 340 (FIG. 1) to enable rotational, reciprocating, and/or other motional driving of cutting tool 330. Cutting tool 330 further includes a distal working tip 334 that extends distally from inner shaft 328.

Outer shaft 326 is disposed about inner shaft 328 and operably engaged with proximal collar 324 (e.g., fixedly or in any other suitable manner) such that actuation of proximal collar 324 translates outer shaft 326 about and relative to inner shaft 328. Proximal collar 324, in turn, is operably mounted on proximal hub 323 and configured for rotation, translation, or both rotation and translation relative to proximal hub 323. More specifically, proximal collar 324 may be operably coupled with proximal hub 323 via a threading engagement, a cam follower engaged within a helical channel, or in any other suitable manner such that rotation of proximal collar 324 relative to proximal hub 323 translates proximal collar 324 along proximal hub 323. As an alternative to rotational actuation of proximal collar 324, proximal collar 324 may be slidably disposed about proximal hub 323 to enable translational actuation of proximal collar 324 along proximal hub 323. In such sliding configurations, a suitable locking mechanism may be provided to fix proximal collar 324 in a desired longitudinal position relative to proximal hub 323.

Regardless of the particulars of the operable coupling of proximal collar 324 with proximal hub 323, outer shaft 326 is operably engaged with proximal collar 324 and inner shaft 328 is fixedly engaged with proximal hub 323 with cutting tool 330 extending therethrough such that actuation of proximal collar 324 relative to proximal hub 323 thereby moves outer shaft 326 relative to and about inner shaft 328 and cutting tool 330. In aspects, rather than manual manipulation of proximal collar 324, movement of outer shaft 326 relative to inner shaft 328 may be motor driven, e.g., via motor 340 or another motor disposed within handle 310 (see FIG. 1).

Figures 5A, 5B, 5C:
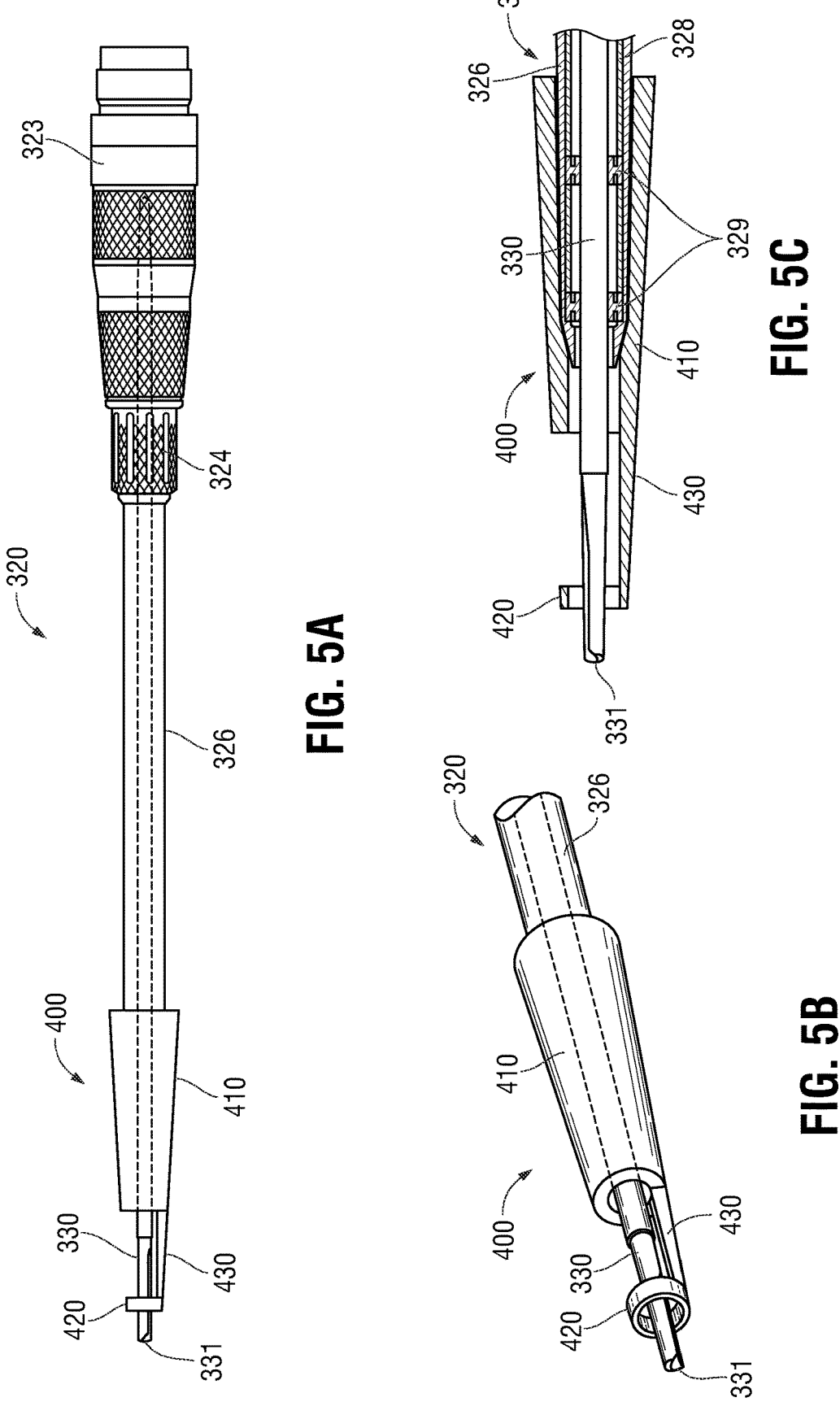
FIG. 5A is a side view of the powered surgical cutting device of FIG. 1 including the retractable shield attached thereto and disposed in a retracted position.
FIG. 5B is a perspective view of the distal portion of the powered surgical cutting device of FIG. 1 including the retractable shield attached thereto and disposed in a retracted position.
FIG. 5C is a longitudinal, cross-sectional view of the distal portion of the powered surgical cutting device of FIG. 1 including the retractable shield attached thereto and disposed in a retracted position.

Continuing with reference to FIGS. 4A-5C, retractable shield 400 is engaged about outer shaft 326 and may be integrally formed therewith or removable therefrom, e.g., via threaded engagement, luer-lock engagement, press-fit engagement, snap-fit engagement, or other suitable releasable locking engagement. Further, retractable shield 400 may extend about a distal length of outer shaft 326 (as shown), may extend about a substantial portion of the length of outer shaft 326, a majority of the length of outer shaft 326, or entirety of the length of outer shaft 326. Notwithstanding, with retractable shield 400 engaged about outer shaft 326, actuation of proximal collar 324 relative to proximal hub 323 moves outer shaft 326 relative to and about inner shaft 328 to thereby move retractable shield 400 relative to inner shaft 328 and cutting tool 330 to vary the position of retractable shield 400 relative to cutting tool 330. More specifically, retractable shield 400 is movable relative to cutting tool 330 between one or more retracted positions (FIGS. 4A-4C), wherein distal tip 331 of cutting tool 330 does not protrude distally beyond a distal most extent of retractable shield 400, and one or more extended positions (FIGS. 5A-5C), wherein distal tip 331 of cutting tool 330 extends distally from the distal most extent of retractable shield 400. In aspects, outer shaft 326 is stationary relative to inner shaft 328 (or omitted entirely) and retractable shield 400 is operably coupled, directly or indirectly, to, proximal collar 324 such that actuation of proximal collar 324 relative to proximal hub 323 moves retractable shield 400 relative to cutting tool 330 between the one or more retracted positions (FIGS. 4A-4C) and/or the one or more extended positions (FIGS. 5A-5C).

Retractable shield 400 includes a proximal body 410 coupled to (e.g., formed as a single piece with, formed separately and attached to, or otherwise coupled to) at least a portion of outer shaft 326, a distal ring 420 distally spaced from proximal body 410, and an arm 430 interconnecting proximal body 410 and distal ring 420 with one another. In aspects, retractable shield 400 is integrally formed from a single piece of material, although other configurations are also contemplated. Proximal body 410 receives cutting tool 330 therethrough, substantially coaxially, and extends at least semi-annularly about outer shaft 326 and cutting tool 330 (in aspects, fully annularly). Arm 430, on the other hand, extends from proximal body 410 to distal ring 420 in spaced, substantially parallel orientation relative to cutting tool 330 without substantially surrounding cutting tool 330. Thus, the portion of cutting tool 330 disposed between proximal body 410 and distal ring 420 is exposed about a substantial portion (e.g., at least 50%) of the annular perimeter thereof. Distal ring 420 is coaxially disposed about cutting tool 330 and, in at least some positions of retractable shield 400, is configured to receive cutting tool 330 at least partially therethrough. In aspects, rather than the entirety of retractable shield 400 moving as detailed herein, arm 430 and distal ring 420 may be movable relative to proximal body 410.

Figure 6:
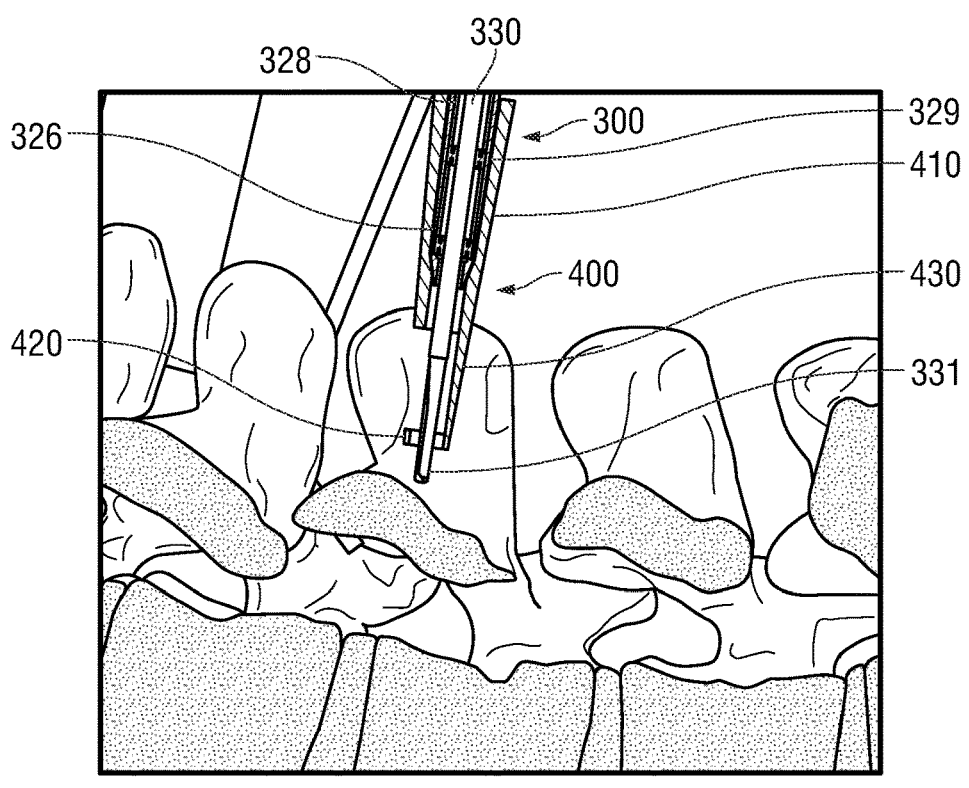
FIG. 6 is a cross-sectional view illustrating use of the powered surgical cutting device of FIG. 1 for cutting spinal tissue with the retractable shield attached to the powered surgical cutting device and disposed in a retracted position.

Referring to FIG. 6, in conjunction with FIGS. 1 and 5A-5C, with retractable shield 400 disposed in a retracted position, wherein cutting tool 330 extends distally through distal ring 420 such that distal tip 331 thereof is exposed distally of retractable shield 400, surgical cutting device 300 may be advanced distally such that cutting tool 330 is urged distally into tissue to cut tissue, e.g., via the rotation and/or reciprocation of cutting tool 330. Notably, the depth of cutting may still be controlled based upon the retracted position of retractable shield 400, with distal ring 420 of retractable shield 400 functioning as a depth limiting stop. That is, with retractable shield 400 positioned such that cutting tool 330 extends a relatively large distance distally through distal ring 420, cutting tool 330 can be utilized to cut deeper into tissue while, with retractable shield 400 positioned such that cutting tool 330 extends a relatively small distance distally through distal ring 420, cutting tool 330 can only be utilized for relatively shallow cutting into tissue. As shown in FIG. 6, cutting tool 330 may be utilized, for example, to bore or drill into spinal bone.

Figure 7:
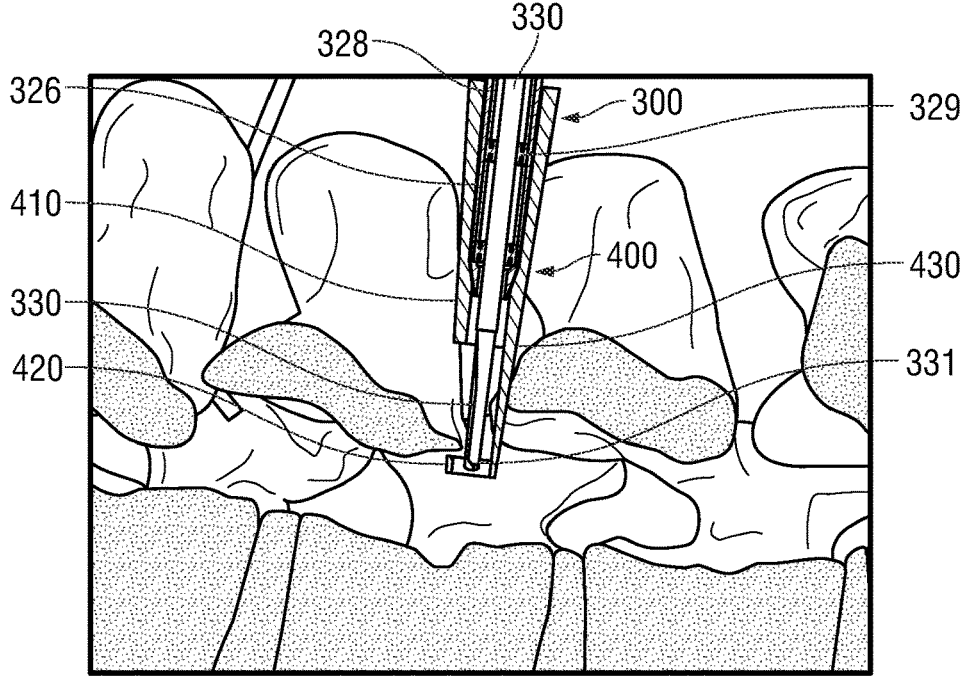
FIG. 7 is a cross-sectional view illustrating use of the powered surgical cutting device of FIG. 1 for cutting spinal tissue with the retractable shield attached to the powered surgical cutting device and disposed in an extended position.

Turning to FIG. 7, in conjunction with FIGS. 1 and 4A-4C, with retractable shield 400 disposed in an extended position, wherein cutting tool 330 does not extend distally beyond distal ring 420 and, thus, such that distal tip 331 is not exposed distally of retractable shield 400, tissue distally of distal tip 331 is protected from being cut even where surgical cutting device 300 is advanced distally toward tissue. However, surgical cutting device 300 may be moved laterally such that cutting tool 330 is advanced transversely relative to tissue to cut tissue, e.g., via rotation and/or reciprocation of cutting tool 330. Such transverse cutting is enabled via the substantially exposed annular perimeter of cutting tool 330 even in an extended position of retractable shield 400. As shown in FIG. 7, cutting tool 330 may be utilized, for example, to transversely cut spinal bone, e.g., to shave or otherwise shape bone.

Figure 8A:
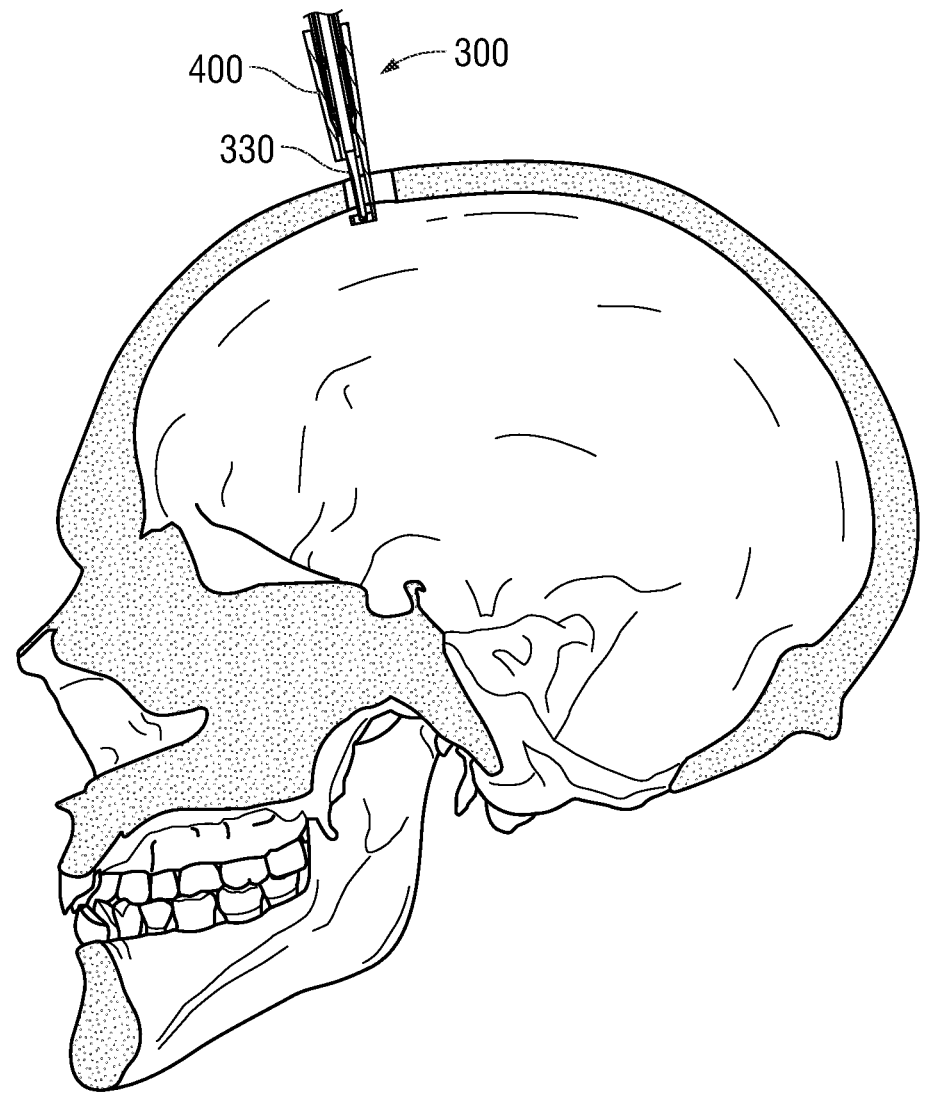
FIG. 8A is a cross-sectional view illustrating use of the powered surgical cutting device of FIG. 1 for cutting cranial tissue.
Figure 8C:
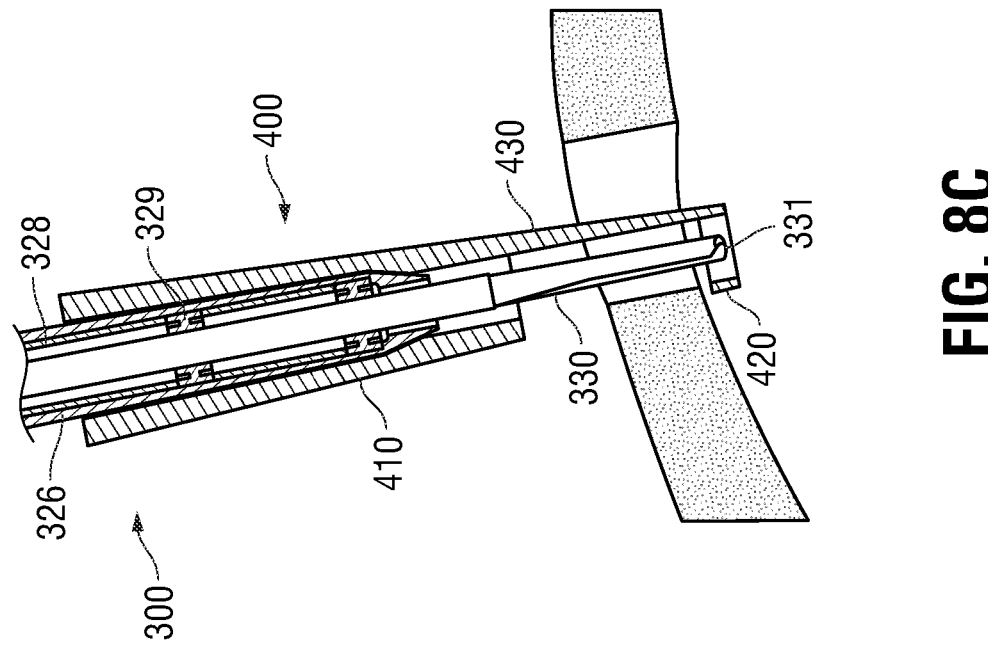
FIGS. 8B and 8C are cross-sectional views illustrating use of the powered surgical cutting device of FIG. 1 for cutting cranial tissue with the retractable shield attached to the powered surgical cutting device and disposed in retracted and extended positions, respectively.
Figure 8B:
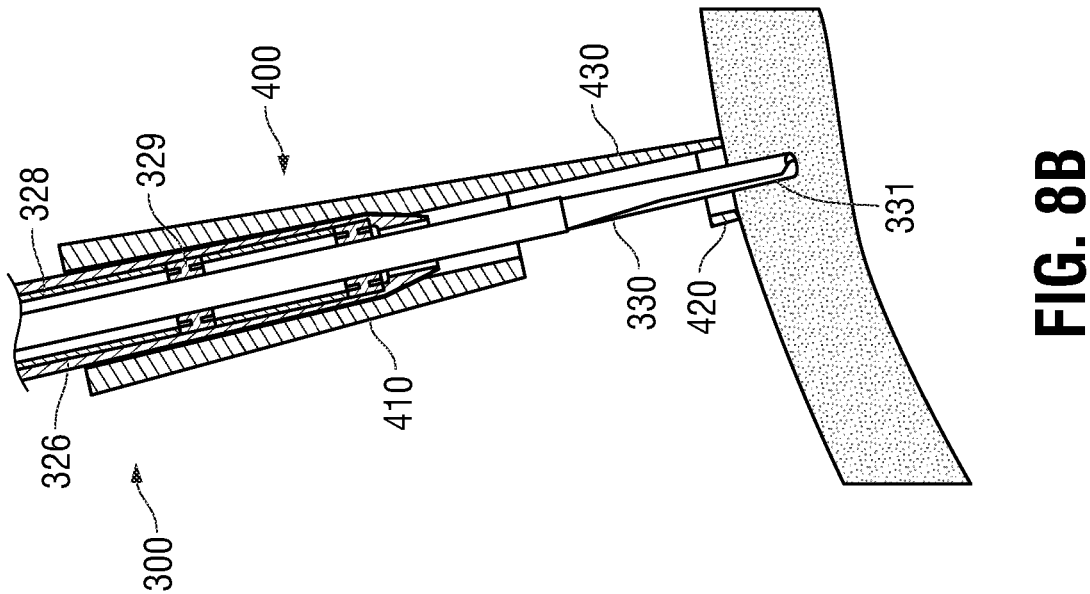

Referring to FIGS. 1 and 8A-8C, surgical cutting device 300 may also be utilized to cut cranial bone. More specifically, as shown in FIG. 8B, with retractable shield 400 disposed in a retracted position, cutting tool 330 may be advanced distally through cranial bone to establish an initial access opening. Retractable shield 400 may be positioned in a desired retracted position during this initial drilling through cranial bone so as to provide appropriate depth control, thus inhibiting cutting tool 330 from reaching internal tissue, e.g., brain tissue. As shown in FIG. 8C, once the initial access opening has been created, retractable shield 400 may be moved to an extended position to enable transverse cutting of cranial bone in a desired pattern, e.g., to enable removal of a section of cranial bone to provide suitable access to internal tissue, e.g., brain tissue.

Figure 9A:
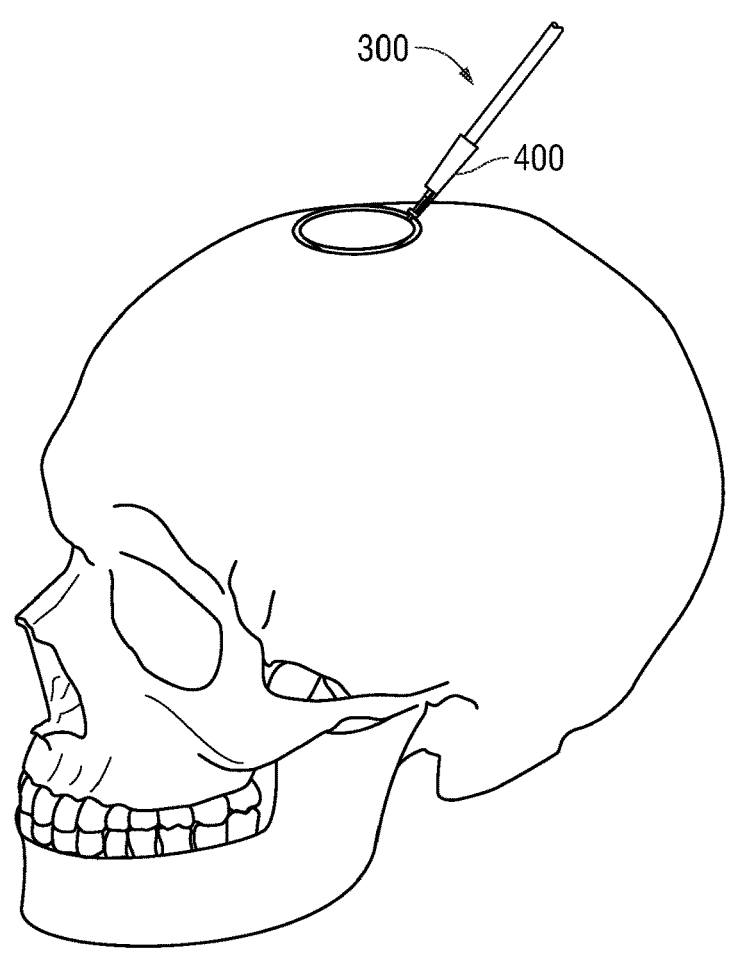
FIGS. 9A and 9B are perspective and cross-sectional views, respectively, illustrating further use of the powered surgical cutting device of FIG. 1 for cutting cranial tissue.
Figure 9B:
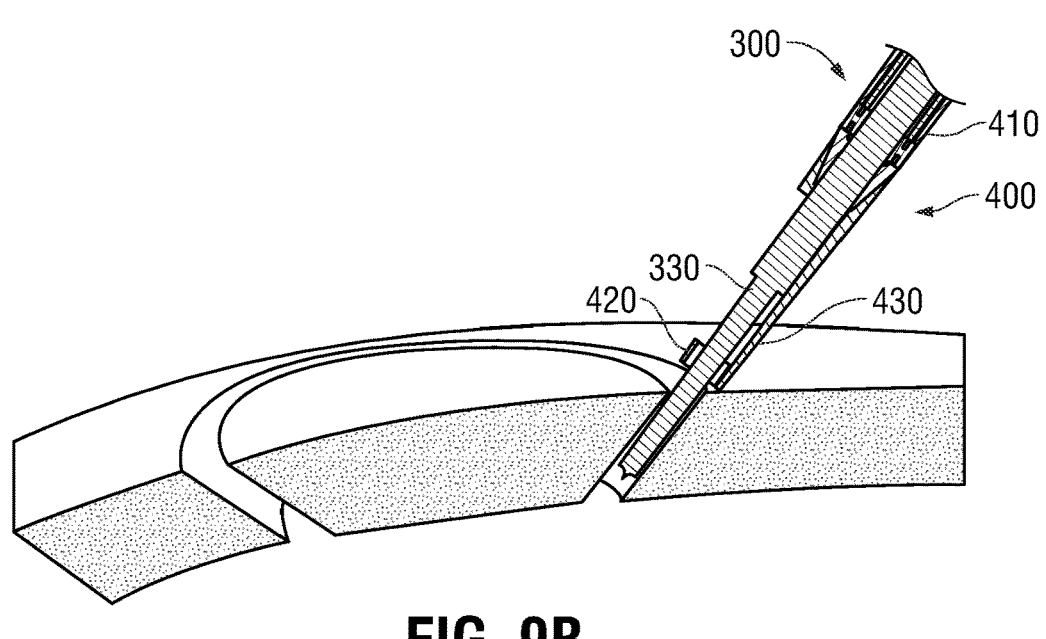
Figure 10A:
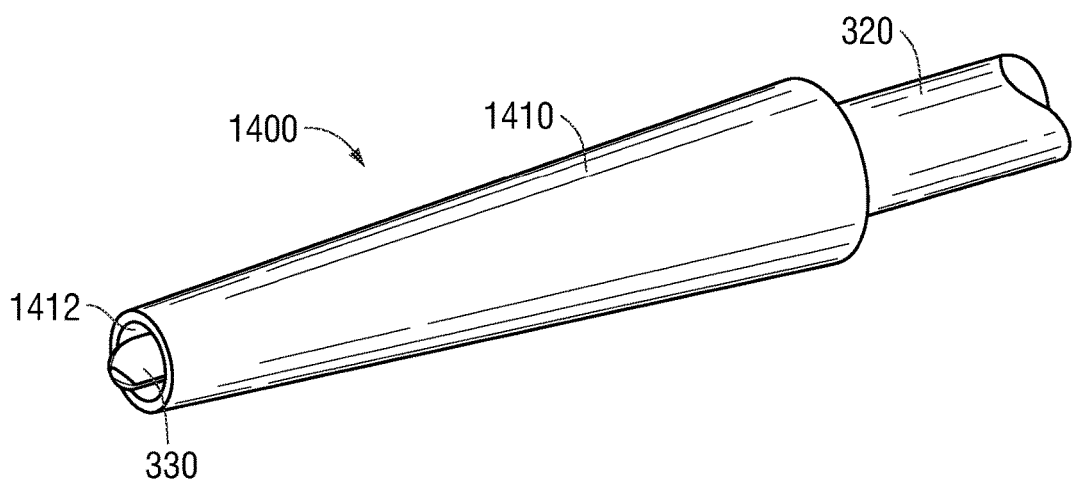
FIGS. 10A and 10B are perspective and cross-sectional views, respectively, of the distal portion of the powered surgical cutting device of FIG. 1 including another retractable shield in accordance with the present disclosure attached thereto and disposed in an extended position.
Figure 10B:
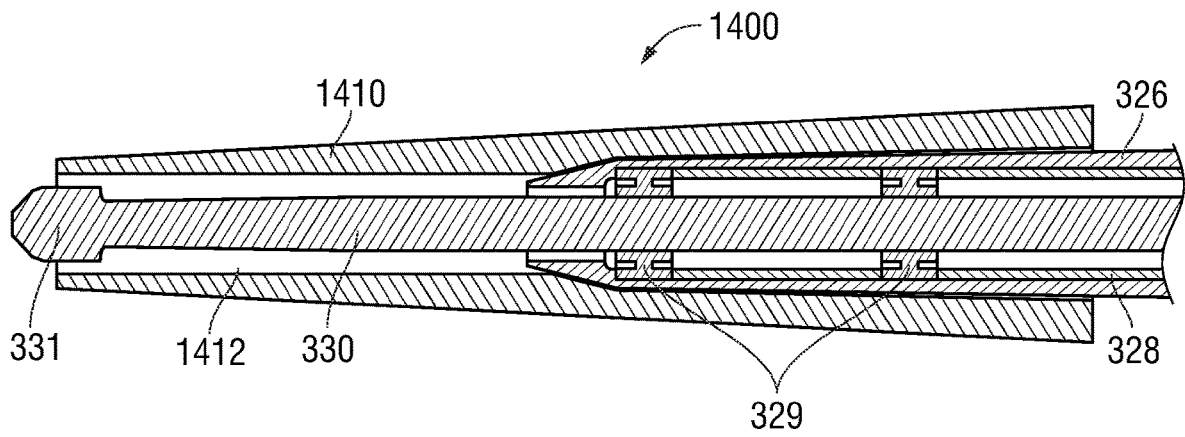
Figure 11A:
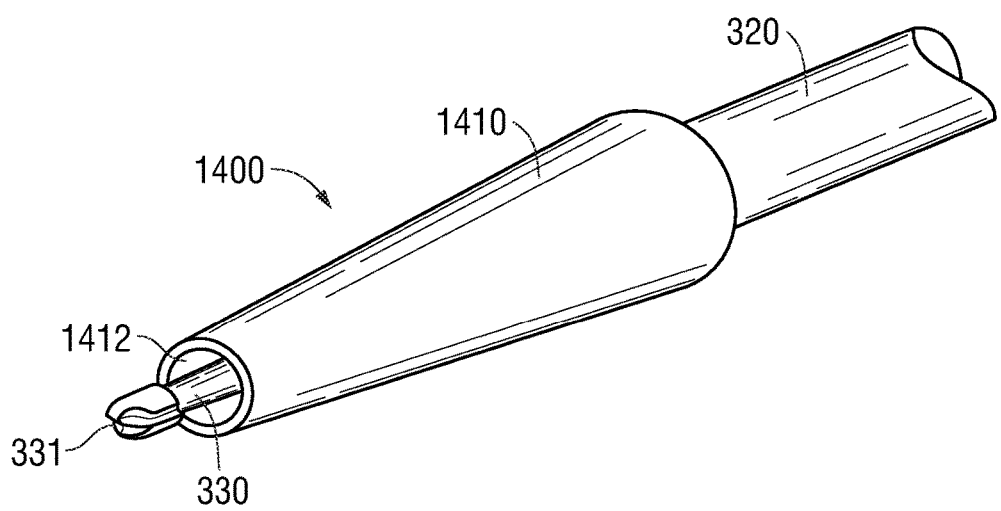
FIGS. 11A and 11B are perspective and cross-sectional views, respectively, of the distal portion of the powered surgical cutting device of FIG. 1 including the retractable shield of FIGS. 10A and 10B in accordance with the present disclosure attached thereto and disposed in a retracted position.
Figure 11B:
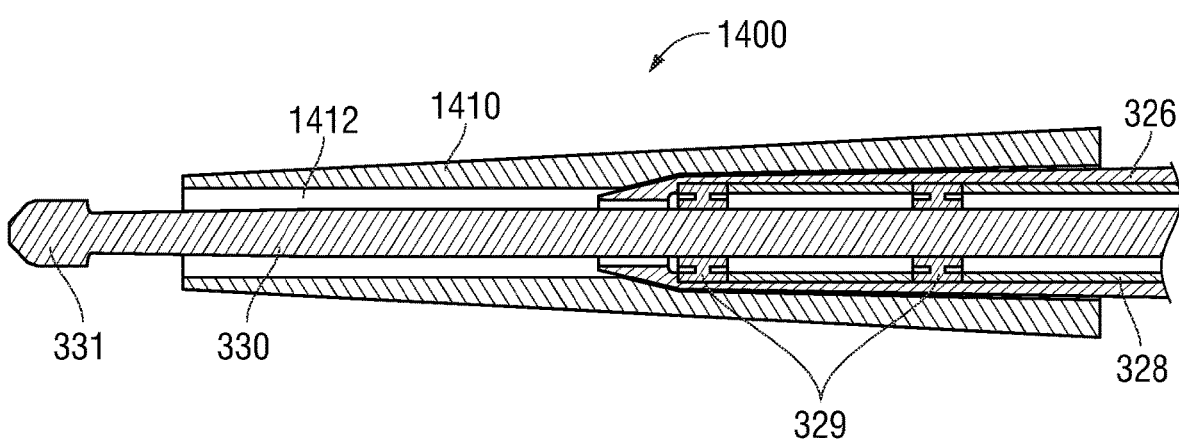

With reference to FIGS. 9A and 9B, rather than positioning retractable shield 400 in an extended position to transversely cut tissue, e.g., cranial bone, retractable shield 400 may be disposed in a depth limiting retracted position such that cutting tool 330 may be angled and transversely advanced (while maintaining the angle) to cut-out a portion of cranial bone having an inwardly angled outer peripheral edge (in an exterior-to-interior direction) such that the portion of cranial bone surrounding the cut-out opening also defines an inwardly-angled perimeter (in an exterior-to-interior direction). Such a configuration may facilitate subsequent replacement and/or securement of the cut-out portion after the underlying surgical task(s) are complete. This technique may be aided by maintaining distal ring 420 of retractable shield 400 in contact with the external surface of cranial bone to act as a support and/or guide.

FIGS. 10A-11B illustrate another retractable shield 1400 in accordance with the present disclosure. Retractable shield 1400 is similar to retractable shield 400 (FIGS. 4A-5C) except that, rather than providing a proximal body and distal ring interconnected by an arm, retractable shield 1400 includes a conical body 1410 extending to the distal extend of retractable shield 1400. Thus, a longitudinal passage 1412 of body 1410 that coaxially surrounds cutting tool 330 functions similarly as distal ring 420 of retractable shield 400 (see FIGS. 4A-5C).

Figure 12:
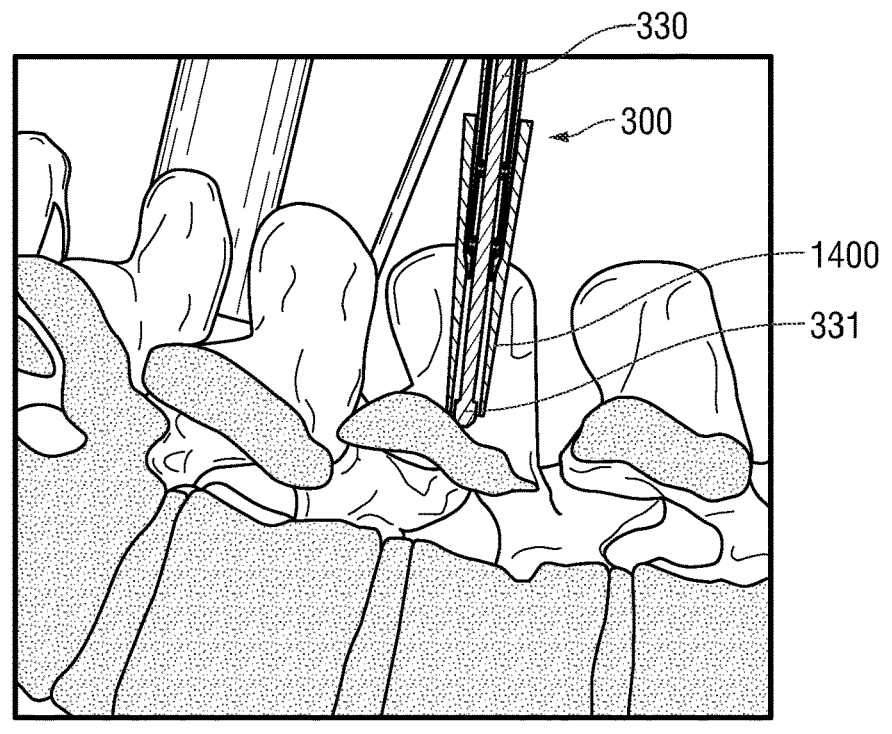
FIGS. 12 and 13 are cross-sectional views illustrating use of the powered surgical cutting device of FIG. 1 for cutting cranial tissue with the retractable shield of FIGS. 10A and 10B attached to the powered surgical cutting device and disposed in extended and retracted positions, respectively.
Figure 13:
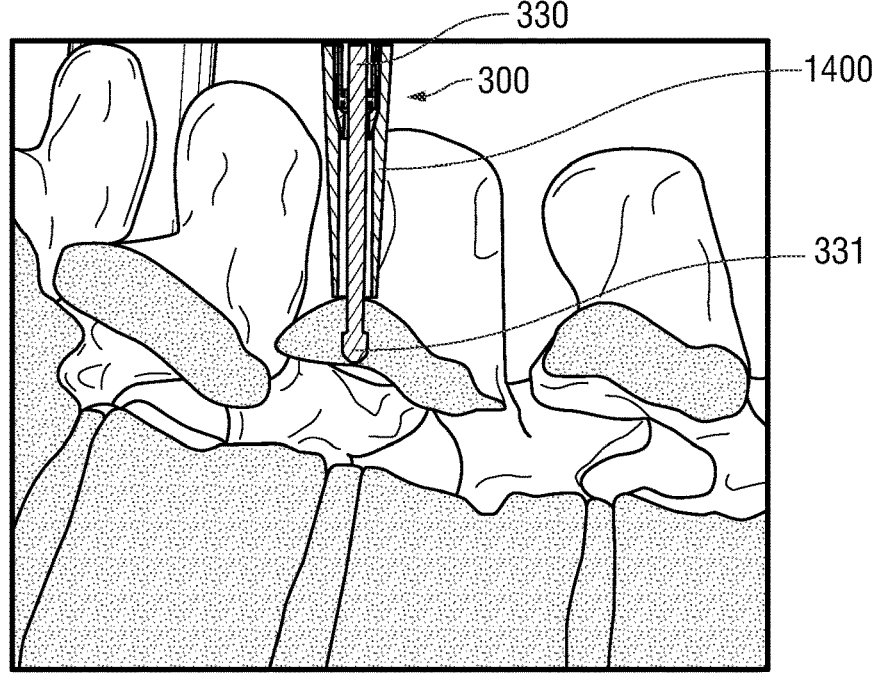

With additional reference to FIGS. 12 and 13, retractable shield 1400 may be extended or retracted to a desired position to provide cutting depth control. More specifically, in a more extended position of retractable shield 1400 (FIG. 12), cutting tool 330 can only be utilized for relatively shallow cutting into tissue, e.g., spinal bone. In a more retracted position of retractable shield 1400 (FIG. 13), cutting tool 330 can drill into tissue, e.g., spinal bone, to a relatively greater depth. Retractable shield 1400 may also be utilized, for example, to perform the cranial bone cutting technique detailed above with reference to FIGS. 9A and 9B and/or for other purposes.

Turning to FIGS. 14-17, in aspects, retractable shield 400 may further include one or more sensors 600. Although described herein with respect to retractable shield 400, sensor(s) 600 may similarly be incorporated into retractable shield 1400 (FIG. 10A) or any other suitable retractable shield. Sensor(s) 600 may be disposed on distal face 610 of retractable shield 400 defined by distal ring 420 and/or arm 430. Sensor(s) 600 may be disposed on substantially all of distal face 610 or only a portion thereof; where multiple sensors 600 are provided, the sensors 600 may be disposed on different portions of distal face 610 or may be otherwise positioned relative to one another. Regardless of the particular number and configuration of the one or more sensors 600, providing the one or more sensors 600 in connection with retractable shield 400 enables the one or more sensors 600 to be operably (and movably) positioned relative to cutting tool 330 and/or tissue to facilitate sensing and, thus, tissue cutting based thereon, as detailed below.

The one or more sensors 600 may include, for example, an image sensor (e.g., to enable real time video imaging of a field of view extending distally from retractable shield 400), an ultrasound sensor (e.g., to enable real time ultrasound imaging of a field of view extending distally from retractable shield 400), a nerve monitoring sensor (e.g., to enable sensing of electrical signals to detect the presence and/or location of nerves distally of retractable shield 400), an electrical impedance and/or other electrical characteristic sensor (e.g., to measure tissue electrical conductivity (and/or other electrical properties) of tissue distally of retractable shield 400 to enable determination of tissue type), a force/pressure sensor (e.g., to measure force or pressure applied to tissue distally of retractable shield 400 to distinguish hard tissue (such as bone) from soft tissue), and/or other suitable sensors. Sensor(s) 600 may be coupled to control circuitry 620 (where multiple sensors 600 are provided, collective or separate control circuitry 620 may be provided), which may be disposed within handle 310 (as shown), shaft assembly 320, retractable shield 400, console 100, another unit (e.g., surgical display system 700 (FIG. 15)), and/or in the cloud or across multiple devices. Control circuitry 620 provides power to sensor(s) 600, controls operation thereof, and receives sensed data from sensor(s) 600 to enable processing such sensed data to provide a suitable output. Control circuitry 620 may include, for example, a field programmable gate array (FPGA), digital signal processor (DSP), central processing unit (CPU), microprocessor, multiples thereof, combinations thereof, or any other suitable logic processor(s) adapted to execute algorithms, perform calculations, and/or implement sets of instructions stored in local or remote memory(s).

Figures 14, 15:
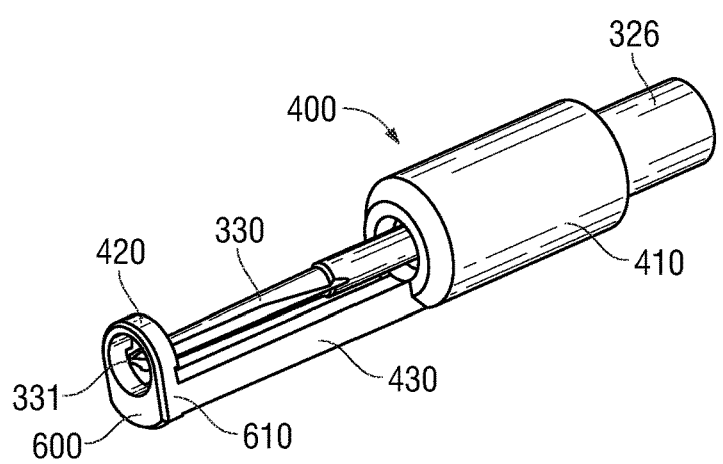
FIG. 14 is a perspective view of the distal portion of the powered surgical cutting device of FIG. 1 including a sensing retractable shield in accordance with the present disclosure attached thereto and disposed in an extended position.
FIG. 15 is a schematic illustration of the powered surgical cutting device of FIG. 1 including the sensing retractable shield of FIG. 14 operably connected to a surgical display system.

As shown in FIG. 15, where the one or more sensors 600 are imaging sensors (video or ultrasound, for example, although other image sensors such as thermal imagers, infrared imagers, etc. are also contemplated), control circuitry 620 may connect to surgical display system 700 to enable display of the real time images sensed by sensor(s) 600. In this manner, the clinician may visualize the surgical site (e.g., the field distally of retractable shield 400) to enable determination of what tissue to cut, what tissue to avoid, the depth of tissue cutting, etc. In aspects, machine learning algorithms associated with control circuitry 620 and/or surgical display system 700 may be utilized to process the image data and determine tissue type and/or other features of tissue to enable, for example: highlighting of different or certain types of tissue (e.g., bone versus soft tissue); emphasizing tissue margins or transitions between tissue types and/or tissue and open space; indicating hidden anatomical structures below other tissue layers; indicating distances to different tissues or other structures; etc.

Other sensor(s) 600 may similarly be utilized, additionally or alternatively, to enhance the display of information provided to a clinician on surgical display system 700. For example, where a nerve monitoring sensor is provided, the location of or an indication or nearby nerves in the field may be indicated on the display; where an electrical impedance and/or other electrical characteristic sensor is provided, the type of tissue detected (bone versus soft tissue, for example) may be indicated on the display; where a force/pressure sensor is provided, the force applied and/or type of tissue determined based upon force feedback may be indicated on the display. Similarly as above, machine learning may be utilized to enhance the information provided by sensor(s) 600 such as, for example, to facilitate tissue type determination, determining a location of an anatomical structure (nerve, blood vessel, etc.), determining the presence/absence of an anatomical structures, etc.

As an alternative or in addition to facilitating the visual display of information for the clinician, e.g., on surgical display system 700, sensor(s) 600 may be utilized to provide other outputs and/or enable feedback based control. For example, control circuitry 620 may be configured to output an audible (e.g., via a speaker), visual (e.g., via an LED), tactile (e.g., via a vibration generator), and/or other suitable output upon detecting a particular condition such as, for example, nearby soft tissue, nerves, other anatomical structures, etc. The output may be provided via an output device of handle 310, of console 100, and/or of any other suitable device.

Figure 16A:
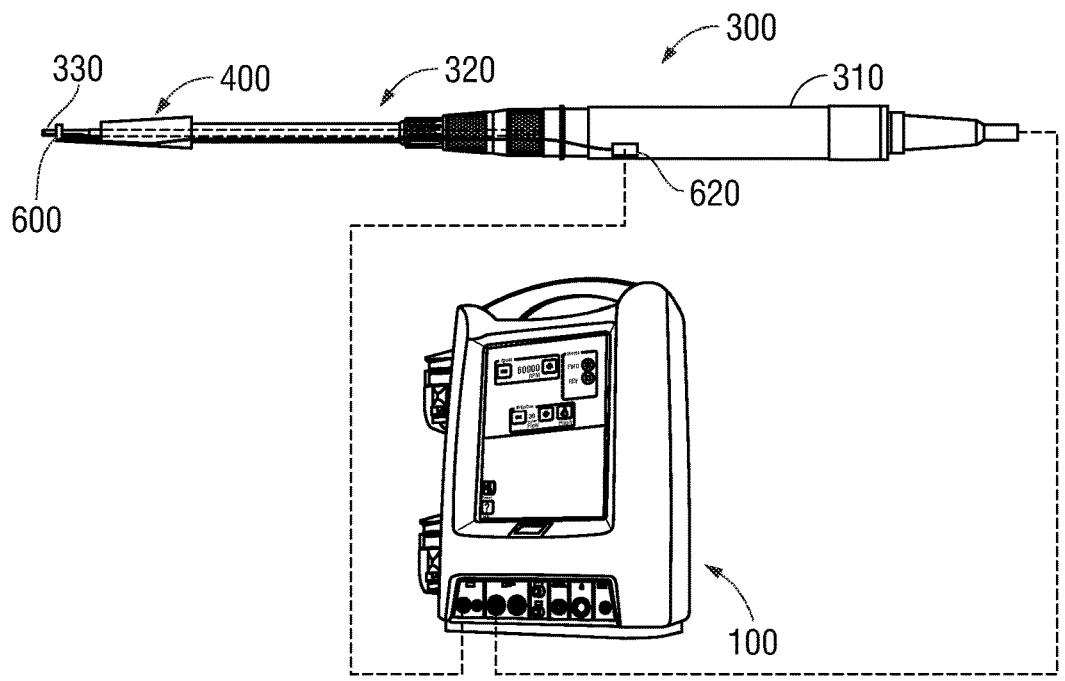
FIGS. 16A and 16B illustrate difference configurations of operably connecting the powered surgical cutting device of FIG. 1 including the sensing retractable shield of FIG. 14 with the console of FIG. 1.
Figure 16B:
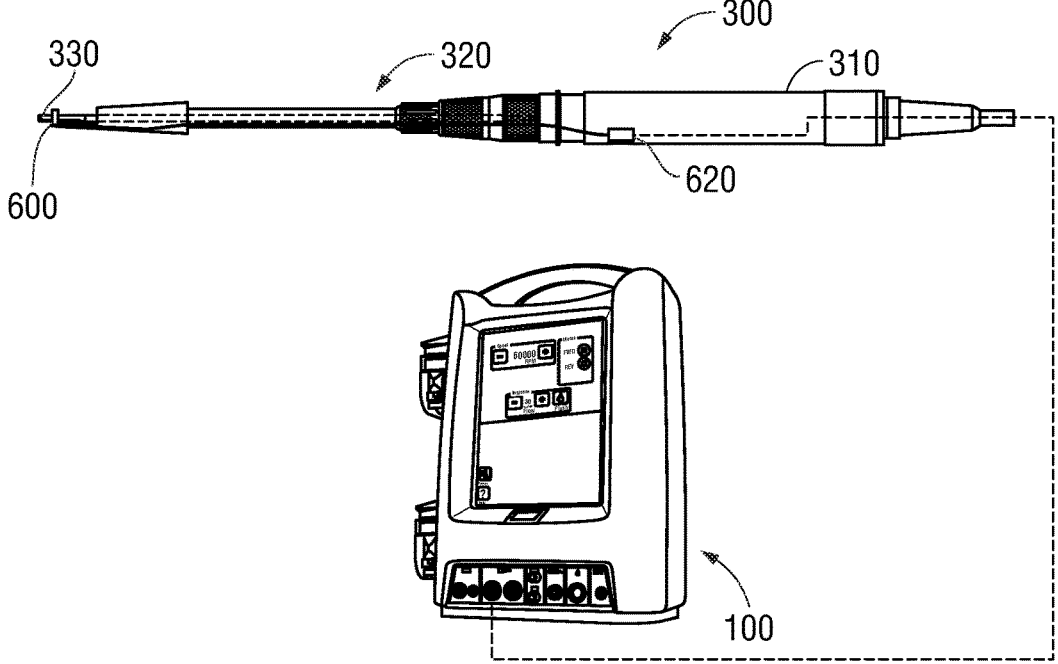
Figure 17:
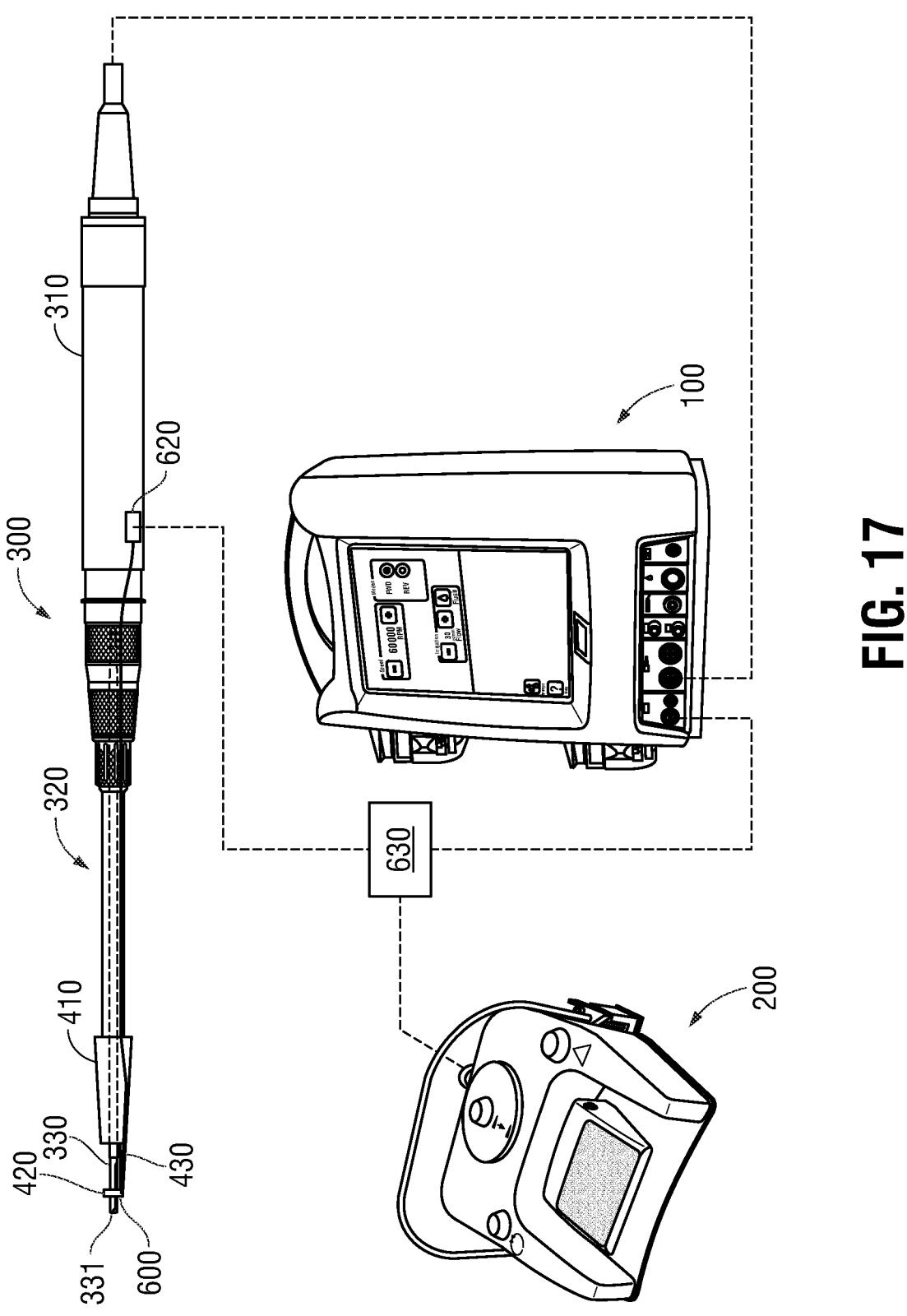
FIG. 17 illustrates operable connection between the powered surgical cutting device of FIG. 1 including the sensing retractable shield of FIG. 14 with the console and footswitch of FIG. 1.

Turning to FIGS. 16A and 16B, control circuitry 620 may be configured to communicate with console 100 separately from the connection of handle 310 with console (see FIG. 16A), via the connection of handle 310 with console 100 (FIG. 16B), or in any other suitable manner. With reference to FIG. 17, in other configurations, control circuitry 620 may be configured to communicate with switching circuitry 630 disposed within or otherwise associated with footswitch 200 to control the input from footswitch 200 to console 100. Regardless of the particular connection arrangement, control circuitry 620 may provide the sensed data (or the processed output based on the sensed data) to enable feedback based control of surgical cutting device 300. For example, where a certain condition is detected by sensor(s) 600 (e.g., the presence of soft tissue or nerves, open space, etc.), feedback regarding the same is communicated from control circuitry 620 to console 100 or switching circuitry 630, thereby enabling console 100 to inhibit activation of surgical cutting device 300 or switching circuitry 630 to interrupt communication of activation signals from footswitch 200 to console 100, respectively, thus preventing activation of surgical cutting device 300, thereby protecting damage to the soft tissue or nerves.

Figure 19:
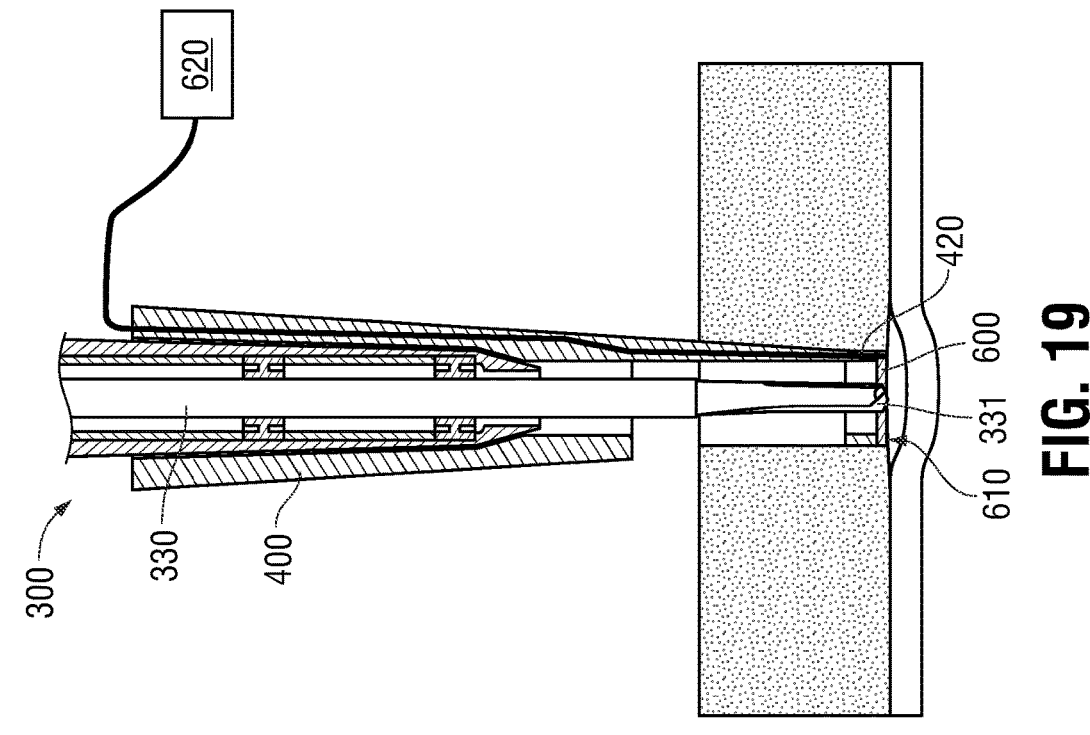
FIGS. 18 and 19 are cross-sectional views of the powered surgical cutting device of FIG. 1 including the sensing retractable shield of FIG. 14 in use cutting tissue.
Figure 18:
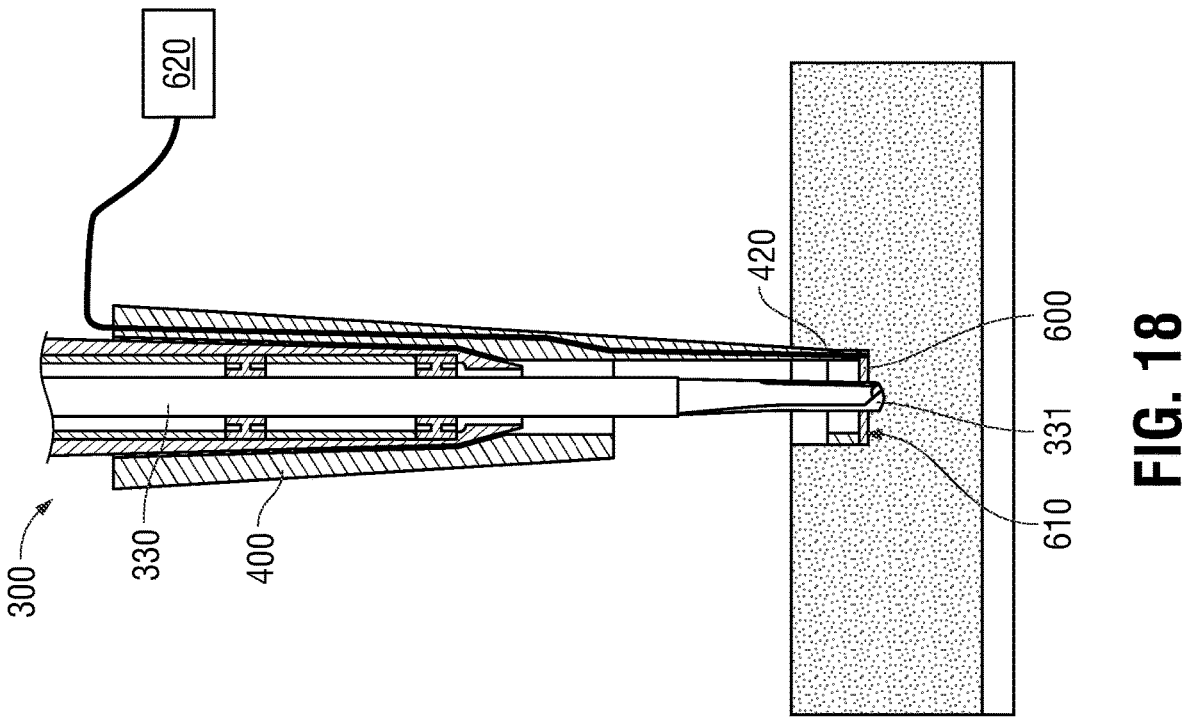
Figure 20:
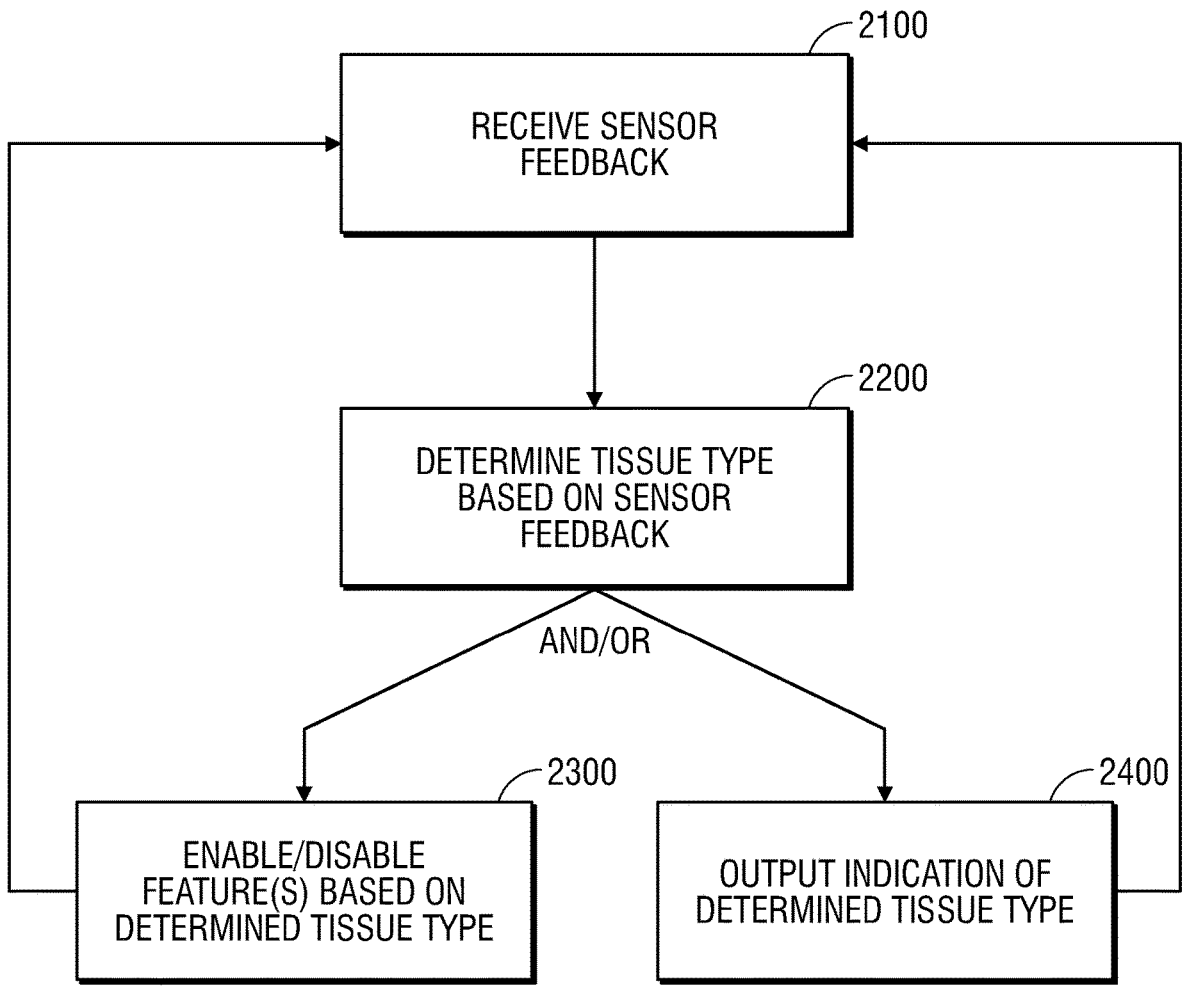
FIG. 20 is a flow diagram of a method in accordance with the present disclosure.

Referring to FIGS. 18-20, and with initial reference to FIG. 18, in use, for example, with retractable shield 400 disposed in an at least partially retracted position wherein at least a portion of cutting tool 330 extends distally through distal ring 420 such that distal tip 331 thereof is exposed distally of retractable shield 400, surgical cutting device 300 may be advanced distally relative to tissue, e.g., bone, such that cutting tool 330 drills through the tissue creating and increasing a depth of a bore through the tissue. As distal tip 331 cuts through the tissue, sensor(s) 600 continuously or periodically senses the field (e.g., the field distally of and/or surrounding retractable shield 400 and distal tip 331) and provides such sensor data to control circuitry 620. Control circuitry 620 receives the sensor feedback, as indicated at step 2100 of FIG. 20, and determines a condition based thereon such as, for example, a tissue type (e.g., bone tissue or soft tissue), as indicated at step 2200 of FIG. 20. Where bone is in the field (see FIG. 18) and, thus, bone is determined at step 2200 of FIG. 20, control circuitry 620 may enable or continue to allow operation of surgical cutting device 300 (FIG. 15), as indicated at step 2300 of FIG. 20 and/or may direct a suitable output indicating that bone is in the field, as indicated at step 2400 of FIG. 20.

On the other hand, once distal tip 331 cuts through the bone, as shown in FIG. 19, sensor(s) 600 sense the soft tissue or open space underlying the bone. Control circuitry 620 receives this sensor feedback (step 2100 of FIG. 20), determines the tissue type as soft tissue or open space (step 2200 of FIG. 20) and, as a result, disables operation of surgical cutting device 300 (FIG. 15), as indicated at step 2300 of FIG. 20 and/or directs a suitable output indicating that soft tissue is in the field, as indicated at step 2400 of FIG. 20. Thus, inadvertently cutting or otherwise damaging soft tissue underling bone tissue to be cut can be avoided.

While several aspects of the present disclosure have been shown in the drawings, it is not intended that the present disclosure be limited thereto, as it is intended that the present disclosure be as broad in scope as the art will allow and that the specification be read likewise. Therefore, the above description should not be construed as limiting, but merely as exemplifications of particular aspects. Those skilled in the art will envision other modifications within the scope and spirit of the claims appended hereto.

What is claimed is:

1. A surgical cutting device, comprising:
a handle;
a shaft assembly extending distally from the handle, the shaft assembly including at least one shaft;
a cutting tool extending at least partially through the shaft assembly, the cutting tool extending distally from the shaft assembly and including a distal cutting tip configured to cut tissue along a longitudinal axis defined through the cutting tool and an exposed annular perimeter configured to cut tissue transverse to the longitudinal axis upon lateral movement of the cutting tool, the cutting tool adapted to connect to a motor configured to drive the cutting tool to cut tissue; and
a retractable shield including a body coupled to the shaft assembly, a ring spaced from the body, and an arm interconnecting the body and the ring with one another, the ring and the arm defining a transverse cutting area therebetween, at least one of the retractable shield or the cutting tool movable relative to the other between a retracted position, wherein the distal tip of the cutting tool extends through and distally beyond the ring of the retractable shield to enable the distal tip to cut tissue via the rotation of the cutting tool, and one or more extended positions, wherein the ring of the retractable shield encapsulates the distal tip of the cutting tool to protect the distal tip of the cutting tool and prevent distal engagement with tissue during rotation thereof and restricts the cutting tool to cutting tissue transversally within the transverse cutting area upon activation and lateral movement thereof.

2. The surgical cutting device according to claim 1, wherein the at least one shaft of the shaft assembly includes an inner shaft and an outer shaft.

3. The surgical cutting device according to claim 2, wherein the retractable shield is formed with or engaged to the outer shaft.

4. The surgical cutting device according to claim 3, wherein the inner shaft rotatably supports the cutting tool therein.

5. The surgical cutting device according to claim 3, further comprising a proximal hub fixed relative to the inner shaft and a proximal collar disposed about the proximal hub and operably coupled to the outer shaft such that actuation of the proximal collar relative to the proximal hub moves the outer shaft relative to the inner shaft to thereby move the retractable shield relative to the cutting tool between the retracted position and the one or more extended positions.

6. The surgical cutting device according to claim 1, wherein the cutting tool is configured to at least one of rotate, reciprocate, or oscillate relative to the shaft assembly to cut tissue.

7. The surgical cutting device according to claim 1, further comprising a motor disposed within the handle, the motor configured to operably connect to the cutting tool and configured to drive movement of the distal tip of the cutting tool.

8. The surgical cutting device according to claim 1, wherein the ring of the retractable shield is coaxially positioned about a longitudinal axis defined through the cutting tool and wherein the arm of the retractable shield is radially spaced from and parallel to the longitudinal axis of the cutting tool.

9. The surgical cutting device according to claim 1, wherein the retractable shield is releasably engageable with the shaft assembly.

10. The surgical cutting device according to claim 1, wherein the shaft assembly and the cutting tool are releasably engageable with the handle.

11. A surgical cutting device, comprising:
a handle;
a shaft assembly extending distally from the handle, the shaft assembly including at least one shaft;
a cutting tool extending at least partially through the shaft assembly, the cutting tool extending distally from the shaft assembly and including a distal cutting tip configured to cut tissue along a longitudinal axis defined through the cutting tool and an exposed annular perimeter configured to cut tissue transverse to the longitudinal axis upon lateral movement of the cutting tool, the cutting tool adapted to connect to a motor configured to drive the cutting tool to cut tissue;
a retractable shield defining a distal face surrounding an opening extending through at least a portion of the retractable shield, the retractable shield defining a transverse cutting area therein, the retractable shield coupled to the shaft assembly and at least one of the retractable shield or the cutting tool movable relative to the other between a retracted position, wherein the distal tip of the cutting tool extends through and distally beyond the opening and distally from the retractable shield to enable the distal tip to cut tissue via the rotation of the cutting tool, and one or more extended positions, wherein the retractable shield encapsulates the distal tip of the cutting tool to protect the distal tip of the cutting tool and prevent distal engagement with tissue during rotation thereof and restricts the cutting tool to cutting tissue transversally within the transverse cutting area upon activation and lateral movement thereof, and a sensor disposed on the distal face of the retractable shield.

12. The surgical cutting device according to claim 11, wherein the sensor is a video or ultrasound image sensor.

13. The surgical cutting device according to claim 11, wherein the sensor is a nerve sensor, an impedance sensor, or a force sensor.

14. The surgical cutting device according to claim 11, wherein the retractable shield includes a body coupled to the shaft assembly, a ring distally spaced from the body, and an arm interconnecting the body and the ring with one another, the opening extending through the ring and the distal face defined on at least one of the ring or the arm.

15. The surgical cutting device according to claim 11, wherein the retractable shield includes a conical body, the opening extending through the conical body and the distal face defined on the conical body.

16. The surgical system according to claim 11, wherein the surgical device includes control circuitry configured to receive sensed data from the sensor and to provide an output based thereon, and wherein the output includes a determination made by the control circuitry based on the sensed data.

17. The surgical system according to claim 16, wherein the determination is a type of tissue.

18. The surgical system according to claim 11, wherein the surgical device includes control circuitry configured to receive sensed data from the sensor and to provide an output based thereon, and wherein the output includes a signal to inhibit activation of the motor or to inhibit input of an activation signal to the motor.

19. The surgical system according to claim 11, wherein the surgical device includes control circuitry configured to receive sensed data from the sensor and to provide an output based thereon, and wherein the output includes image data for at least one of: display on a display screen or use in control of the surgical cutting device.

* * * * *